United States Patent
Fung et al.

(10) Patent No.: US 8,250,013 B2
(45) Date of Patent: Aug. 21, 2012

(54) SYSTEM AND METHOD FOR PRIVACY PRESERVING PREDICTIVE MODELS FOR LUNG CANCER SURVIVAL ANALYSIS

(75) Inventors: Glenn Fung, Madison, WI (US); R. Bharat Rao, Berwyn, PA (US); Sriram Krishnan, Exton, PA (US); Shipeng Yu, Exton, PA (US); Cary Dehing-Oberije, Brunssum (NL); Philippe Lambin, Genappe-Bousval (BE); Dirk de Ruysscher, Tervuren (BE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 820 days.

(21) Appl. No.: 12/353,310

(22) Filed: Jan. 14, 2009

(65) Prior Publication Data

US 2009/0187522 A1      Jul. 23, 2009

Related U.S. Application Data

(60) Provisional application No. 61/022,009, filed on Jan. 18, 2008.

(51) Int. Cl.
*G06F 17/00* (2006.01)
*G06N 5/00* (2006.01)

(52) U.S. Cl. ............... 706/45; 706/14; 706/15; 706/20; 706/21

(58) Field of Classification Search ........................ None
See application file for complete search history.

(56) References Cited

U.S. PATENT DOCUMENTS

| | | | |
|---|---|---|---|
| 6,546,389 B1* | 4/2003 | Agrawal et al. | 1/1 |
| 7,823,207 B2* | 10/2010 | Evenhaim | 726/26 |
| 2005/0125279 A1* | 6/2005 | Wu | 705/10 |
| 2007/0233711 A1* | 10/2007 | Aggarwal et al. | 707/100 |
| 2008/0209568 A1* | 8/2008 | Chang et al. | 726/26 |

OTHER PUBLICATIONS

Chi et al. "Application of Artificial Neural Network-Based Survival Analysis on Two Breast Cancer Datasets", AMIA 2007, pp. 130-134.*
Fung et al. "Finite Newton Method for Lagrangian Support Vector Machine Classification", pp. 1-22. Data Mining Institute Technical Report 02-01, Feb. 2002, pp. 1-22.*
Kou et al. "Privacy Preserving Data Mining of Medical Data Using Data Separation-Based Techniques", Data Science Journal, 2007, pp. 429-434.*
Fan et al. "Variable Selection for Cox's Proportional Model and Frailty Model", The Annals of Statistics, 2002, pp. 74-99.*
Fung et al. "Multicategory Proximal Support Vector Machine Classifiers", Kluwer Academic Publishers, 2004, pp. 1-21.*

(Continued)

*Primary Examiner* — Omar Fernandez Rivas
(74) *Attorney, Agent, or Firm* — Joshua Ryan

(57) ABSTRACT

A computer-implemented method for privacy-preserving data mining to determine cancer survival rates includes providing a random matrix B agreed to by a plurality of entities, wherein each entity i possesses a data matrix $A_i$ of cancer survival data that is not publicly available, providing a class matrix $D_i$ for each of the data matrices $A_i$, providing a kernel $K(A_i, B)$ by each of said plurality of entities to allow public computation of a full kernel, and computing a binary classifier that incorporates said public full kernel, wherein said classifier is adapted to classify a new data vector according to a sign of said classifier.

16 Claims, 7 Drawing Sheets

OTHER PUBLICATIONS

Li et al. "Kernel Cox Regression Models for Linking Gene Expression Profiles to Censored Survival Data", Pacific Symposium on Biocomputing, 2003, 12 pages.*

Oivi L. Mangasarian et al., "Privacy-Preserving Classification of Horizontally Partitioned Data Via Random Kernels," Technical Report 07-02, Data Mining Insititute, Computer Sciences Department, University of Wisconsin, Madison, WI 53706, Sep. 2007, 11 pages.

Glenn Fung et al., "Privacy-Preserving Predictive Models for Lung Cancer Survival Analysis", Proceedings of Siam 2008 Conference on Data Mining, Apr. 24, 2008-Apr. 28, 2008, pp. 40-47, Atlanta Georgia USA.

Hwanja Yu et al., "Privacy-Preserving SVM using Nonlinear Kernels on Horizontally Partitioned Data", Applied Computing 2006. 21st Annual ACM Symposium on Applied Computing, [online] vol. 1, Apr. 23, 2006-Apr. 27, 2006, pp. 603-610, ACM New York, NY USA.

Jaideep Vaidya et al., "Privacy-preserving SVM classification", Knowledge and Information Systems; An International Journal, Springer-Verlag, LO, vol. 14, No. 2, Mar. 24, 2007, pp. 161-178.

Hwanjo Yu et al., "Privacy-Preserving SVM Classification on Vertically Partitioned Data", Advances in Knowledge Discovery and Data Mining Lecture Notes in Computer Science; Lecture Notes in Artificial Intelligence; LNCS, Springer, Berlin, DE, vol. 3918, Jan. 1, 2006, pp. 647-656.

International Search Report of Application U.S. Appl. No. PCT/US2009/00313 dated Sep. 23, 2009.

* cited by examiner

SYSTEM AND METHOD FOR PRIVACY PRESERVING PREDICTIVE MODELS FOR LUNG CANCER SURVIVAL ANALYSIS

CROSS REFERENCE TO RELATED UNITED STATES APPLICATIONS

This application claims priority from "Privacy Preserving Predictive Models for Lung Cancer Survival Analysis", Provisional Application No. 61/022,009 of Fung, et al., filed Jan. 18, 2008, the contents of which are herein incorporated by reference in their entireties.

TECHNICAL FIELD

This disclosure is directed to privacy preserving techniques for use in data mining.

DISCUSSION OF THE RELATED ART

Privacy preserving Data mining (PPDM) is a recent emergent research area that deals with the incorporation of privacy preserving concerns to data mining techniques. Of particular interest is a scenario when the data is horizontally distributed among different institutions, which in the medical domain means that each medical institution (hospitals, clinics, etc.) provides a database containing a complete (or almost complete) subset of item sets (patients). An efficient PPDM algorithm should be able process the data from all the sources and learn data mining/machine learning models that take into account all the information available without sharing explicitly private information among the sources. The ultimate goal of a PPDM model is to perform similarly or identically to a model learned by having access to all the data at the same time.

There has been a push for the incorporation of electronic health records (EHR) in medical institutions worldwide. There is a consensus among health care professionals that the availability of EHR will have several significant benefits for health systems across the world, including: improvement of quality of care by tracking performance on clinical measures, better and more accurate insurance reimbursement, computer assisted diagnosis (CAD) tools, etc. Therefore, an increasing number of hospitals are saving large amounts of data that can be used to build predictive models to assist doctors in the medical decision process for treatment, diagnosis, and prognosis, etc. However, sharing the data across institutions is a challenging and tedious process that also involves a legal and economic burden on the institutions sharing the medical data.

There is recent work that shows the potential of the PPDM approach in medical settings. Most of the available data mining techniques require and assume that there is complete access to all data at all times. This may not be true for example, in an uncentralized distributed medical setting where for each data source or institution, there are local procedures in place to enforce privacy and security of the data. If this is the case, there is a need to use efficient data mining and machine learning techniques that can use data across institutions while complying with the non-disclosure nature of the available data. There are two categories of data partitioning when dealing with distributed setting where PPDM is needed. The first setting is when the data is partitioned vertically, which means that all institutions have some subset of features (predictors, variables) for all the available patients. When this is the case, several techniques have been proposed to address the issue including adding random perturbations to the data. The other popular PPDM setting occurs when the data is partitioned horizontally among institutions, which means that different entities hold the same input features for different groups of individuals. This case have been addressed by privacy-preserving SVMs and induction tree classifiers. There several other recently proposed privacy preserving classifying techniques including cryptographically private SVMs and wavelet-based distortion. However, there is little work in developing implementing PPDM for predictive personalized medicine.

SUMMARY OF THE INVENTION

Exemplary embodiments of the invention as described herein generally include methods and systems for privacy preserving techniques applied to learn survival predictive models for non-small-cell lung cancer patients treated with (chemo) radiotherapy. Real data collected from patients treated on three European institutions in two different countries (the Netherlands and Belgium) was used to test the models. A framework according to an embodiment of the invention enables designing/learning improved predictive models that perform better than the individual models obtained by using local data from only one institution, while addressing the local and international privacy preserving concerns that arise when sharing patient related data. The performance of a technique according to an embodiment of the invention was empirically measured on a real-world clinical application. To the knowledge of the inventors, there is no previous work related to learning survival models for lung cancer radiation therapy addressing PP concerns.

According to an aspect of the invention, there is provided a method for privacy-preserving data mining to determine cancer survival rates, including providing a random matrix B agreed to by a plurality of entities, wherein each entity i possesses a data matrix $A_i$ of cancer survival data that is not publicly available, providing a class matrix $D_i$ for each of the data matrices $A_i$, providing a kernel $K(A_i, B)$ by each of said plurality of entities to allow public computation of a full kernel, and computing a binary classifier that incorporates said public full kernel, wherein said classifier is adapted to classify a new data vector according to a sign of said classifier.

According to a further aspect of the invention, the class matrix D is of size m×m wherein m is a number of data points and has a value +1 on a main diagonal for each survival datum that exceeds a predetermined number of years, and has a value of −1 on said main diagonal for each survival datum that does not exceed the predetermined number of years.

According to a further aspect of the invention, the random matrix B is real valued of size $\bar{m} \times n$, wherein n is a dimensionality of each data point, and $\bar{m} < n$, and each data matrix $A_i$ is of size m×n, wherein m is a number of data points.

According to a further aspect of the invention, the full kernel is $$K(A, B') = K\left(\begin{bmatrix} A_1 \\ A_2 \\ \vdots \\ A_q \end{bmatrix}, B\right) = \begin{bmatrix} K(A_1, B) \\ K(A_2, B) \\ \vdots \\ K(A_q, B) \end{bmatrix},$$

where $q$ is a number of entities.

According to a further aspect of the invention, the classifier is defined as $K(x',B')w-\gamma 0$ wherein w is a vector normal the a hyperplane separating the two classes of the binary classifier, γ determines the location of the separating hyperplane relative to the origin, and K(x', B') is a row vector of K(A, B').

According to a further aspect of the invention, the classifier is solved for using a Newton-Lagrangian method wherein a square of a 2-norm of a slack variable is minimized with weight v/2 wherein v>0 and a distance between bounding planes is measured in an (n+1)-dimensional space of (w,γ) $\in R^{n+1}$.

According to another aspect of the invention, there is provided a method for privacy-preserving data mining to determine cancer survival rates, including providing a random matrix B agreed to by a plurality of entities, wherein each entity i possesses a data matrix $A_i$ of cancer survival rates that is not publicly available, providing a kernel $K(A_i, B)$ by each of said plurality of entities to allow public computation of a full kernel, and maximizing a quantity w'K(x, B') wherein x is a row in one of said data matrices $A_i$ to solve for vector w, wherein said quantity w'K(x, B') is an effect parameter in a survival model that characterizes an effect on said cancer survival rates.

According to a further aspect of the invention, the effect parameters w'xB is an effect parameter of a cox regression model log h(t)=α(t)+w'xB', wherein h(t) is a hazard function and α(t) represents an unspecified baseline hazard function.

According to another aspect of the invention, there is provided a program storage device readable by a computer, tangibly embodying a program of instructions executable by the computer to perform the method steps for privacy-preserving data mining to determine cancer survival rates.

DETAILED DESCRIPTION OF EXEMPLARY EMBODIMENTS

Figure 1:
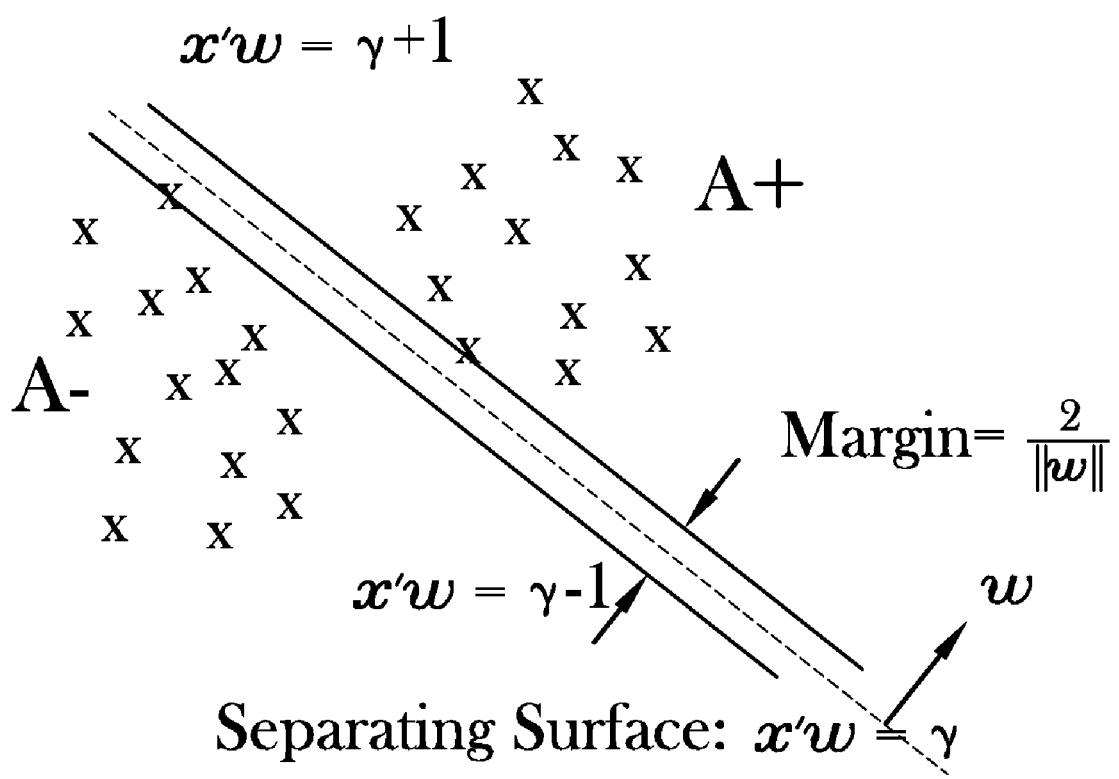
FIG. 1 illustrates a support vector machine, according to an embodiment of the invention.

Exemplary embodiments of the invention as described herein generally include systems and methods for privacy preserving classification techniques in the medical domain. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

Notation

All vectors will be column vectors unless transposed to a row vector by a prime '. For a vector $x \in R^n$ the notation $x_j$ will signify either the j-th component or j-th block of components. The scalar (inner) product of two vectors x and y in the n-dimensional real space $R^n$ will be denoted by x'y. The notation $A \in R^{m \times n}$ will signify a real m×n matrix. For such a matrix, A' will denote the transpose of A, $A_i$ will denote the i-th row or i-th block of rows of A. A vector of ones in a real space of arbitrary dimension will be denoted by e. Thus for $e \in R^m$ and $y \in R^m$ the notation e'y will denote the sum of the components of y. A vector of zeros in a real space of arbitrary dimension will be denoted by 0. For $A \in R^{m \times n}$ and $B \in R^{m \times n}$, a kernel K(A,B') maps $R^{m \times n} \times R^{m \times k}$ into $R^{m \times k}$. In particular, if x and y are column vectors in Rn then, K(y', y) is a real number, K(x',B') is a row vector in $R^k$ and K(A,B') is an m×k matrix. The abbreviation "s.t." stands for "subject to".

Overview of Support Vector Machines

Described in this section is the fundamental classification task that leads to the standard quadratic support vector machine (SVM) formulation that minimizes a quadratic convex function. The task of classifying m points x in the n-dimensional real space $R^n$, represented by the m×n matrix A, according to membership of each point $A_i$ in the classes +1 or −1 is specified by a given m×m diagonal matrix D with ones or minus ones along its diagonal. For this task, the standard support vector machine with a linear kernel AA' is given by the following quadratic program for some v>0:

$$\min_{(w,\gamma,y) \in R^{n+1+m}} ve'y + \frac{1}{2}w'w \qquad (1)$$

$$\text{s.t.} \quad D(Aw - e\gamma) + y \geq e, \ y \geq 0$$

The vector w is normal to the two bounding planes:

$$x'w - \gamma = +1,$$

$$x'w - \gamma = -1, \qquad (2)$$

and γ determines their location relative to the origin. The first plane above bounds the class +1 points and the second plane bounds the class −1 points when the two classes are strictly linearly separable, that is when the slack variable y=0. The linear separating surface is the plane $$x'w = \gamma, \qquad (3)$$

midway between the bounding planes of EQ. (2). If the classes are linearly inseparable then the two planes bound the two classes with a "soft margin" determined by a nonnegative slack variable y, that is:

$$x'w - \gamma + y \geq +1, \text{ for } x' = A_i \text{ and } D_{ii} = +1,$$

$$x'w - \gamma - y \leq -1, \text{ for } x' = A_i \text{ and } D_{ii} = -1. \qquad (4)$$

The 1-norm of the slack variable y is minimized with weight v in EQ. (1). The quadratic term in EQ. (1), which is twice the reciprocal of the square of the 2-norm distance $$\frac{2}{\|w\|}$$

between the two bounding planes of EQ. (2) in the n-dimensional space of w×$R^n$ for a fixed γ, maximizes that distance, often called the "margin". FIG. 1 depicts the points represented by A+ and A−, the bounding planes defined by EQ. (2) with margin $$\frac{2}{\|w\|},$$

and the separating plane of EQ. (3) which separates A+, the points represented by rows of A with $D_{ii}=+1$, from A−, the points represented by rows of A with $D_{ii}=-1$.

Methods of solving quadratic support vector machines are known in the art. According to an embodiment of the invention, a Newton-Lagrangian SVM (NSVM) was used, an algorithm based on an essentially equivalent formulations of this classification task. In this formulation, the square of 2-norm of the slack variable y is minimized with weight v/2 instead of the 1-norm of y as in EQ. (1). In addition, the distance between the planes of EQ. (2) is measured in the (n+1)-dimensional space of $(w,\gamma) \in R^{n+1}$, that is $$\frac{2}{\|(w,\gamma)\|}.$$

Measuring the margin in this (n+1)-dimensional space instead of $R^n$ induces strong convexity and has little or no effect in general on the task. However, it is to be understood that an NSVM is exemplary and non-limiting, and any method for optimizing a quadratic program may be used, such as conjugate gradient methods and primal-dual interior point methods. Commercially available quadratic programming packages may also be suitable.

Privacy Preserving Predicative Models

A privacy preserving application according to an embodiment of the invention uses a technique on random kernel mappings based on two ideas.

1. The use of reduced kernel mappings, where the kernel centers are randomly chosen: instead of using the complete kernel function $K(A,A'):R^{m\times n} \to R^{n\times m}$ as is usually done in kernel methods, one can use a reduced kernel $K(A,B'):R^{m\times n} \to R^{n\times \bar{m}}$, where $BR^{\bar{m}\times n}$ is a completely random matrix with fewer rows than the number of available features, ($\bar{m}<n$).

2. Each entity makes public only a common randomly generated linear transformation of the data given by the matrix product of its privately held matrix of data rows multiplied by the transpose of a common random matrix B for linear kernels, and a similar kernel function for nonlinear kernels. According to an embodiment of the invention, it was assumed that all the available patient data is normalized between 0 and 1 and therefore the elements of B were generated according to a normal distribution with mean zero, variance one and standard deviation one.

Figure 2:
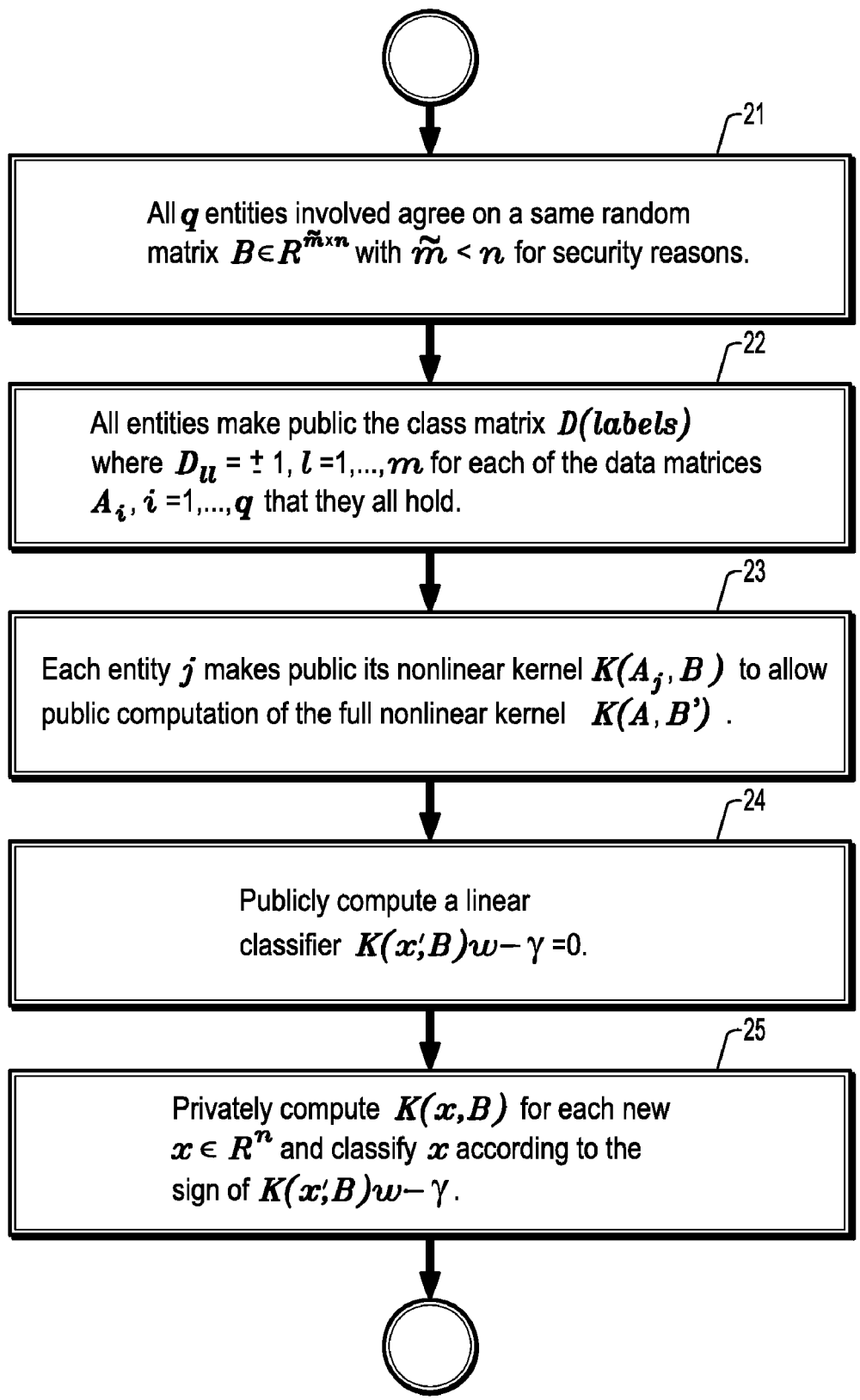
FIG. 2 is a flowchart of a method for privacy preserving data mining, according to an embodiment of the invention.

A privacy preserving support vector machine (PPSVM) algorithm according to an embodiment of the invention is presented in FIG. 2. Referring now to the figure, a method begins at step 21 with all q entities involved agreeing on a same random matrix $B \in R^{\bar{m}\times n}$ with $\bar{m}<n$ for security reasons as justified in the explanation immediately following this algorithm. Then, at step 22, all entities make public the class matrix D(labels) where $D_{ll}=\pm 1$, $l=1,\ldots,m$ for the each of the data matrices $A_i$, $i=1,\ldots,q$ that they all hold. At step 23, each entity j makes public its nonlinear kernel $K(A_j,B)$. This does not reveal $A_j$ but allows the public computation of the full nonlinear kernel:

$$K(A, B') = K\left(\begin{bmatrix} A_1 \\ A_2 \\ \vdots \\ A_q \end{bmatrix}, B\right) = \begin{bmatrix} K(A_1, B) \\ K(A_2, B) \\ \vdots \\ K(A_q, B) \end{bmatrix} \quad (5)$$

A publicly calculated linear classifier $K(x', B)w-\gamma=0$ is computed at step 24 by any linear hyperplane based classification or regression method. Finally, at step 25, for each new $x \in R^n$, obtained by an entity, that entity privately computes $K(x, B)$, from which a nonlinear classifier output is computed from $K(x',B)w-\gamma$, which classifies the given x according to the sign of $K(x',B)w-\gamma$.

The above algorithm works for any kernel with the following associative property:

$$K\left(\begin{bmatrix} C \\ D \end{bmatrix}, F\right) = \begin{bmatrix} K(C, F) \\ K(D, F) \end{bmatrix},$$

which includes, in particular, the case of the linear kernel $K(A,B')=AB'$ which will be used in an embodiment of the invention for simplicity of exposition.

In the above algorithm, no entity j reveals its data nor its components of a new testing data point. When $\bar{m}<n$, there are an infinite number of matrices $A_i \in R^{m_i \times n}$ in the solution set of the equation $A_i B'=P_i$, when B and $P_i$ are given. More formally, this claim is supported by the following proposition, stated and proved in Mangasarian and Wild, "Privacy-Preserving Classification of Horizontally Partitioned Data via Random Kernels", Technical Report 07-02, Computer Sciences Department, University of Wisconsin—Madison, Madison, Wis., 2007, the contents of which are herein incorporated by reference in their entirety.

Proposition: Given the matrix product $P_i'=A_i B' \in R^{m_i \times \bar{m}}$, where $A_i \in R^{m_i \times n}$ is unknown and B is a known matrix in $R^{\bar{m}\times n}$ with $\bar{m}<n^-m<n$, there are an infinite number of solutions, including:

$$\binom{n}{\bar{m}}^{m_i} = \left(\frac{n!}{(n-\bar{m})!\bar{m}!}\right)^{m_i}$$

possible solutions $A_i \in R^{m_i \times n}$ to the equation $A_i B'=P_i$. Furthermore, the infinite number of matrices in the affine hull of these $$\binom{n}{\bar{m}}^{m_i}$$

matrices also satisfy $A_i B'=P_i$.

Cox Regression.

Cox regression, or the Cox propositional-hazards model, is one of the most popular algorithms for survival analysis. Apart from a classification algorithm which directly deals with binary or multi-class outcomes, Cox regression defines a semi-parametric model to directly relate the predictive variables with the real outcome, which is in general a survival time (e.g., in years).

The primary object of interest in survival analysis is the survival function also called survivorship function, conventionally denoted S, which is defined as $$S(t)=Pr(T>t),$$

where t is some time, T is a random variable denoting the time of death, and Pr is a probability. The survival function is the probability that the time of death T is later than some specified time t. Usually one assumes S(0)=1, although it could be less than 1 if there is the possibility of immediate death or failure. The survival function is non-increasing: $S(u) \leq S(t)$ if u>t. This reflects the notion that survival at a later age is only possible if surviving all younger ages. The survival function is usually assumed to approach zero as age increases without bound, i.e., $S(t) \to 0$ as $t \to \infty$.

The hazard function is defined as the event rate at time t conditional on survival until time t or later:

$$h(t) = \lim_{\Delta t \to 0} \frac{Pr[t \leq T < t+\Delta t \mid T \geq t]}{\Delta t}$$
$$= -\frac{S'(t)}{S(t)}.$$

The hazard function must be nonnegative, $\lambda(t) \geq 0$, and its integral over must be infinite, but is not otherwise constrained. The hazard function is a representation of the distribution of survival times, which assesses the instantaneous risk of demise at time t, conditional on survival to that time.

Survival models can be considered to include two parts: the underlying hazard function, describing how hazard (risk) changes over time, and an effect parameters, describing how hazard relates to other factors, such as the choice of treatment, in a typical medical example. The proportional hazards assumption is the assumption that effect parameters multiply hazard: for example, if taking drug X halves your hazard at time 0, it also halves your hazard at time 1, or time 0.5, or time t for any value of t. The effect parameters estimated by any proportional hazards model can be reported as a hazard ratio. The hazard ratio is the effect on this hazard rate of a difference, such as group membership (for example, treatment or control, male or female), as estimated by regression models which treat the log of the hazard rate as a function of a baseline hazard $\alpha(t)$ and a linear combination of explanatory variables w'x.

Cox regression assumes that the proportional hazards assumption holds, in which case it is possible to estimate the effect parameter(s) without any consideration of the hazard function. The Cox regression model assumes a linear model for the log-hazard, or a multiplicative model for the hazard:

$$\log h(t) = \alpha(t) + w'x, \quad (6)$$

where x denotes the covariates for each observation, and the baseline hazard $\alpha(t)$ is unspecified. This model is semi-parametric because while the baseline hazard can take any form, the covariates enter the model linearly. Now, given any two observations (i.e. patient survival times) $x_i$ and $x_j$, from the definition of hazard function, one can obtain:

$$\frac{h(t_i)}{h(t_j)} = \exp[w'(x_i - x_j)],$$

which is independent of time t. The baseline hazard $\alpha(t)$ also does not affect the hazard ratio. This is why the Cox model is a proportional-hazards model.

It has been shown that even though the baseline hazard is unspecified, the Cox model can still be estimated by the method of partial likelihood. It is also possible to extract an estimate of the baseline hazard after having fit the model.

The main idea of a privacy preserving SVM according to an embodiment of the invention is to perform a random mapping of the original predictive variables into a new space, and then perform standard SVM on the new space. Since in Cox regression the covariates are also linearly combined in the survival model, one can also apply the same idea and, according to an embodiment of the invention, develop a privacy preserving Cox regression. Given the random matrix B and assuming a linear kernel, EQ. (6) is modified to:

$$\log h(t) = \alpha(t) + w'xB', \quad (7)$$

and $$\frac{h(t_i)}{h(t_j)} = \exp[w'(x_i - x_j)B'],$$

or, more generally, $$\log h(t) = \alpha(t) + w'K(x, B'),$$
$$\frac{h(t_i)}{h(t_j)} = \exp[w'(K(x_i, B') - K(x_j, B'))].$$

The covariates x can be extracted from the data matrices A, and the weight vector w' can be found using maximum likelihood estimates, which can be found by, e.g., using any Newtonian method, To knowledge of the inventors, this is for the first time that privacy preserving techniques have been applied to survival analysis methods.

Application: 2-Year Survival Prediction for Non-Small Cell Lung Cancer Patients

Radiotherapy, combined with chemotherapy, is the treatment of choice for a large group of non-small cell lung cancer (NSCLC) patients. The treatment is not restricted to patients with mediastinal lymph node metastasis, but is also indicated for patients who are inoperable because of their physical condition. In addition, the original marginal role of radiotherapy and chemotherapy for NSCLC patient survival has changed into one of importance. Improved radiotherapy treatment techniques allow an increase of the radiation dose, while at the same time more effective chemoradiation schemes are being applied. These developments have lead to an improved outcome in terms of survival. Although the introduction of fluorodeoxyglucose positron emission tomography (FDG-PET) scans has enabled more accurate detection of positive lymph nodes and distant metastases, leading to stage migration, the TNM staging system is still highly inaccurate for the prediction of survival outcome for this group of patients. In summary, an increasing number of patients are being treated successfully with (chemo) radiation, but an accurate estimation of the survival probability for an individual patient, taking into account the patient, tumor, treatment characteristics and offering the possibility for treatment decision-making, is currently unavailable.

At present, generally accepted prognostic factors for inoperable patients are performance status, weight loss, presence of comorbidity, use of chemotherapy in addition to radiotherapy, radiation dose and tumor size. For other factors such as gender and age, the literature shows inconsistent results, making it impossible to draw definitive conclusions. In these studies CT-scans were used as the major staging tool. However, the increasing use of FDG-PET scans offers the possibility to identify and use new prognostic factors. In a recent study, it was shown that the number of involved nodal areas quantified by PET-CT scans was an important prognostic factor. The inventors performed this retrospective study to develop and validate several prediction models for 2-year survival of NSCLC patients, treated with (chemo) radiotherapy, taking into account all known prognostic factors. To the best of the inventor's knowledge, this is the first study of prediction models for NSCLC patients treated with (chemo) radiotherapy Patient Population.

Between May 2002 and January 2007, a total number of 455 inoperable NSCLC patients, stage I-IIIB, were referred to a clinic to be treated with curative intent. Clinical data of all these patients were collected retrospectively by reviewing the clinical charts. If PET was not used as a staging tool, patients were excluded from the study. This resulted in the inclusion of 399 patients. The primary gross tumor volume ($GTV_{primary}$) and nodal gross tumor volume ($GTV_{nodal}$) were calculated, as delineated by the treating radiation oncologist, using a commercially available radiotherapy treatment planning system. The sum of $GTV_{primary}$ and $GTV_{nodal}$ resulted in the GTV. For patients treated with sequential chemotherapy these volumes were calculated using the post-chemotherapy imaging information. The creation of the volumes was based on PET and CT information only, and bronchoscopic findings were not taken into account. The number of positive lymph node stations was assessed by the nuclear medicine specialist using either an integrated FDG-PET-CT scan or a CT-scan combined with an FDG-PET-scan. T-stage and N-stage were assessed using pre-treatment CT, PET and mediastinoscopy when applicable. For patients treated with sequential chemotherapy stages, the number of positive lymph node stations was assessed using prechemotherapy imaging information.

In addition, a smaller number of patients treated at two other centers were also collected for this study. There are respectively 112 and 40 patients from the two hospitals, and the same set of clinical variables as the first set patients were measured.

Radiotherapy Treatment Variables.

No elective nodal irradiation was performed and irradiation was delivered 5 days per week. Radiotherapy planning was performed with a Focus (CMS) system, taking into account u lung density and according to ICRU 50 guidelines. There were four different radiotherapy treatment regimes applied for these patients in this retrospective study, therefore to account for the different treatment time and number of fractions per day, the equivalent dose in 2 Gy fractions, corrected for overall treatment time (EQD2,T), was used as a measure for the intensity of chest radiotherapy. Adjustment for dose per fraction and time factors were made as follows:

$$(EQD2, T) = D\left(\frac{d+\beta}{2+\beta}\right) - \gamma \max(0, T - T_k), \quad (6)$$

where D is the total radiation dose, d is dose per fraction, $\beta$=10 Gy, T is overall treatment time, $T_k$ is the accelerated repopulation kick-off time, which, according to an embodiment of the invention, is 28 days, and $\gamma$ is the loss in dose per day due to repopulation, which according to an embodiment of the invention, is 0.66 Gy/day.

Experimental Setup.

A test of a method according to an embodiment of the invention focuses on 2-year survival prediction for these NSCLC patients, which is the most interesting prediction from clinical perspective. The survival status was evaluated in December 2007. The following 6 clinical predictors are used to build the prediction models: gender (two groups: male/female), WHO performance status (three groups: 0/1/$\geq$2), lung function prior to treatment (forced expiratory volume, in the range of 17~139), number of positive lymph node stations (five groups: 0/1/2/3/$\geq$4), natural logarithm of GTV (in the range of −0.17~6.94), and the equivalent dose corrected by time (EQD2,T) from EQ. (6). The mean values across patients are used to impute the missing entries if some of these predictors are missing for certain patients. To account for the very different number of patients from the three sites, a subset of the first set of patients were selected for the following study. In the following, the names "MAASTRO", "Gent" and "Leuven" are used to denote the data from the three different centers.

For the SVM methods, since they can only deal with binary outcome, only the patients with a 2-year follow-up were used to create an outcome with +1 meaning they survived 2 years, and −1 meaning they didn't survive 2 years. This setting leads to 70, 37 and 23 patients for the MAASTRO, Gent and Leuven sets, respectively. For the Cox regression methods, one can potentially use all the patients with the exact number of survived years, and do right censoring for those patients who are still alive. Under this setting there are 80, 85 and 40 patients for MAASTRO, Gent and Leuven, respectively.

Under the privacy preserving setting, one is interested in assessing the predictive performance of a model combining the patient data from the three centers together, compared to the models trained based on each of these centers. The data combination needs to be performed in such a way that sensitive information is not uncovered. Therefore, the following 4 models were trained under each configuration for the experiments:

(1) PP model: Apply a privacy preserving techniques according to an embodiment of the invention and train a model using combined data from the three centers.
(2) MAASTRO model: Train a model using only the MAASTRO training patients.
(3) Gent model: Train a model using only the Gent training patients.
(4) Leuven model: Train a model using only the Leuven training patients.

For each of the configurations, the percentage of training patients is varied in each of the centers, and the Area Under the ROC Cue (AUC) is reported for the test patients. Note that the testing was performed using all the test patients from all centers.

Results

Figure 3:
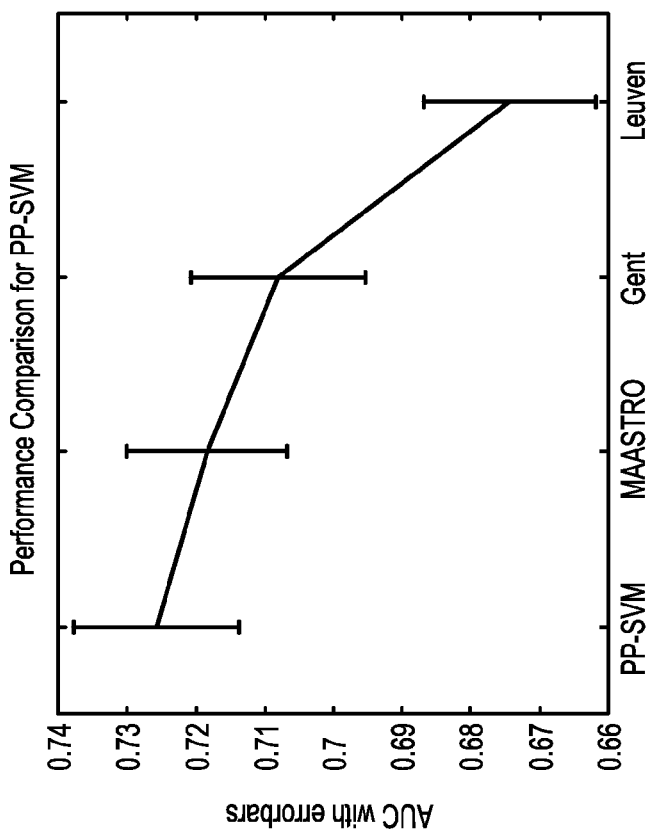
FIG. 3 shows AUC comparison results for privacy preserving SVM models, according to an embodiments of the invention.
Figure 3:
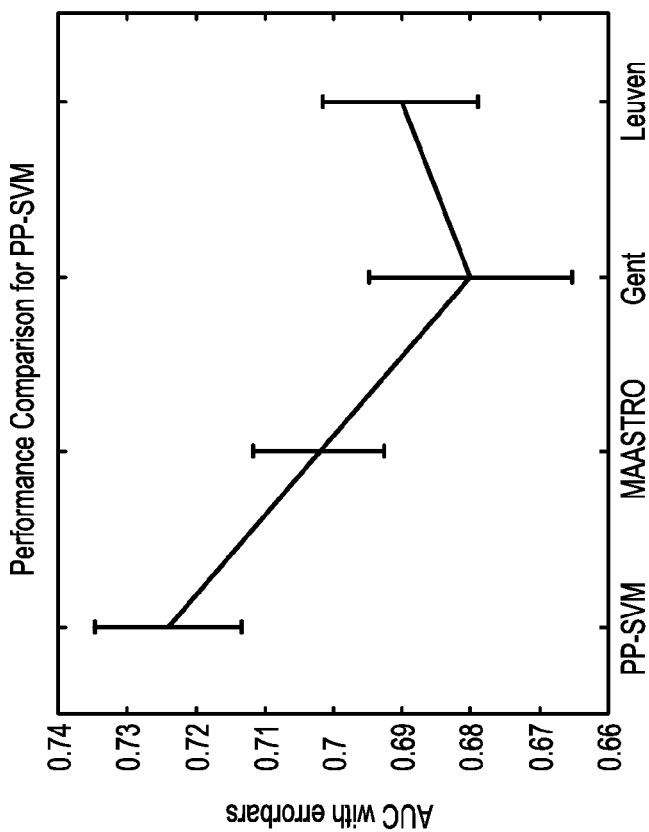

FIG. 3 shows AUC comparison results for privacy preserving SVM models, with 40% (left) and 60% (right) training patients. The other percentages yield similar results. The error bars are over 100 runs with random split of training/test patients for each center, and each time a random B matrix of dimensionality 5×6 is used for the PP-SVM models. As can be seen, the PP-SVM models achieve the best performance compared to other single center based models. This is mainly because PP-SVM models are able to use more data in model training, at the same time without violating the privacy regulations. When the training percentages are increased, all models will improve (compare FIG. 3, right to left), and the single-center based models have a higher improvement. However the PP-SVM models still perform the best.

Figure 4:
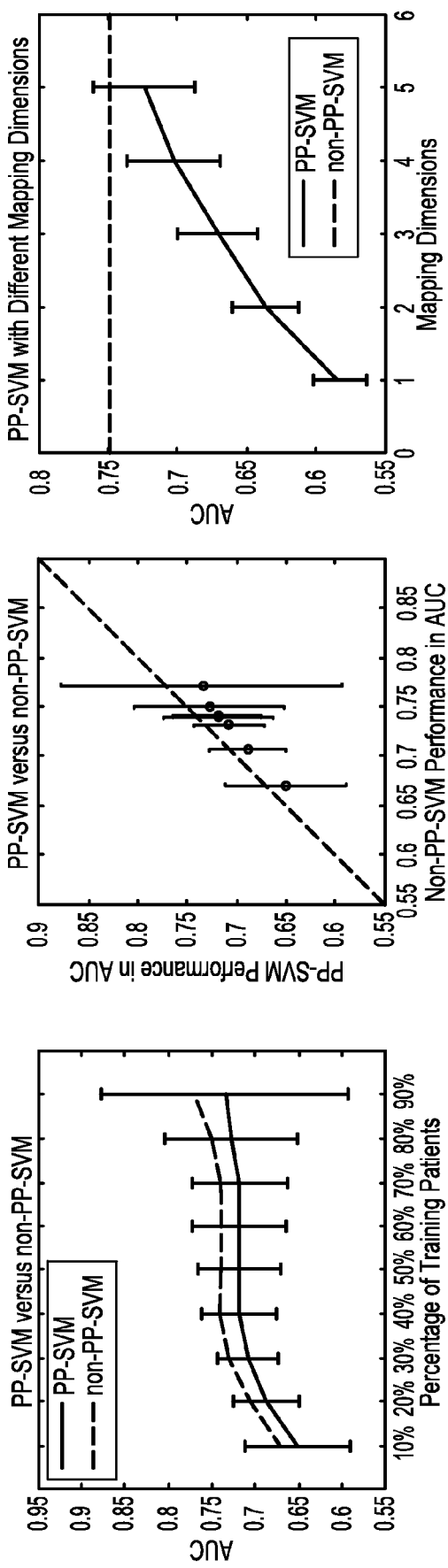
FIG. 4 presents an AUC comparison between PP-SVMs according to embodiments of the invention and non PP-SVMs models.

A PP-SVM according to an embodiment of the invention will have a performance loss compared to a non PP-SVM model, which explicitly combines all the training patients from different centers and does not preserve privacy. This is because in a PP-SVMs according to an embodiment of the invention, a random matrix B projects each patient into a lower dimensional space (for privacy preserving purposes), and thus leads to information loss. To empirically evaluate how much performance loss a PP-SVM according to an embodiment of the invention has, a more extensive comparison is shown in FIG. 4. FIG. 4 presents an AUC comparison between PP-SVMs according to embodiments of the invention and non PP-SVMs which explicitly use all the training data from different centers, and thus upper-bound the predictive performance of a PP-SVM according to an embodiment of the invention. On the left is shown the comparison with different percentages of the training/test splits, and as can be seen, the gaps between a PP-SVM according to an embodiment of the invention and non PPSVMs are not large. This indicates that a PP-SVM according to an embodiment of the invention can achieve similar predictive performance while satisfying the privacy preserving requirement. The scatter plot in the middle is another way to visualize these results. On the right the mapping dimensions $\tilde{m}$ are varied for the B matrix used in PP models, and as expected, a larger $\tilde{m}$ yields better predictive performance. Therefore, in practice one normally chooses $\tilde{m}=n-1$ to maximize the performance of the PP models, which still perfectly satisfy the privacy preserving requirements. From this comparison it may be seen that there are large error bars for different B matrices.

Figure 5:
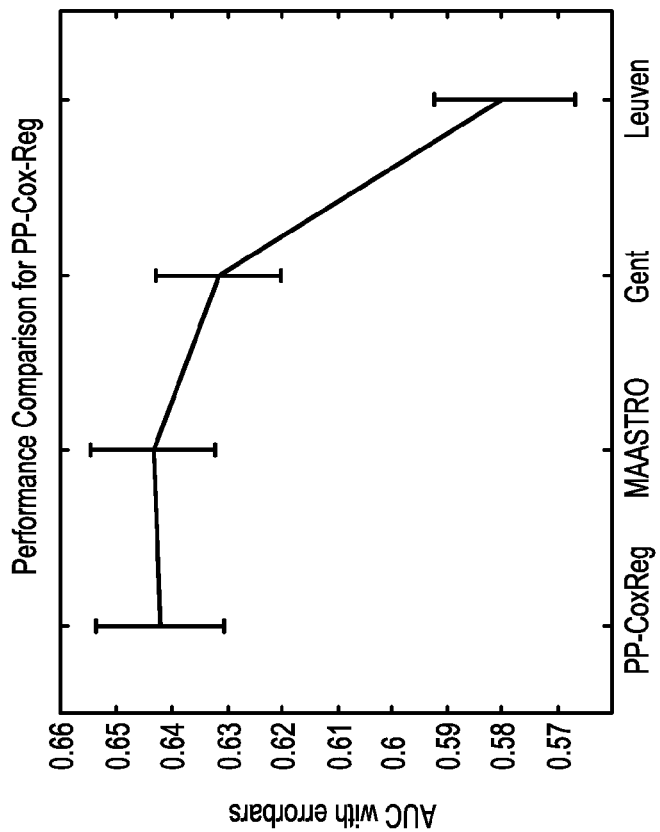
FIG. 5 depicts an AUC comparison results for privacy preserving Cox regression models, according to an embodiments of the invention.
Figure 5:
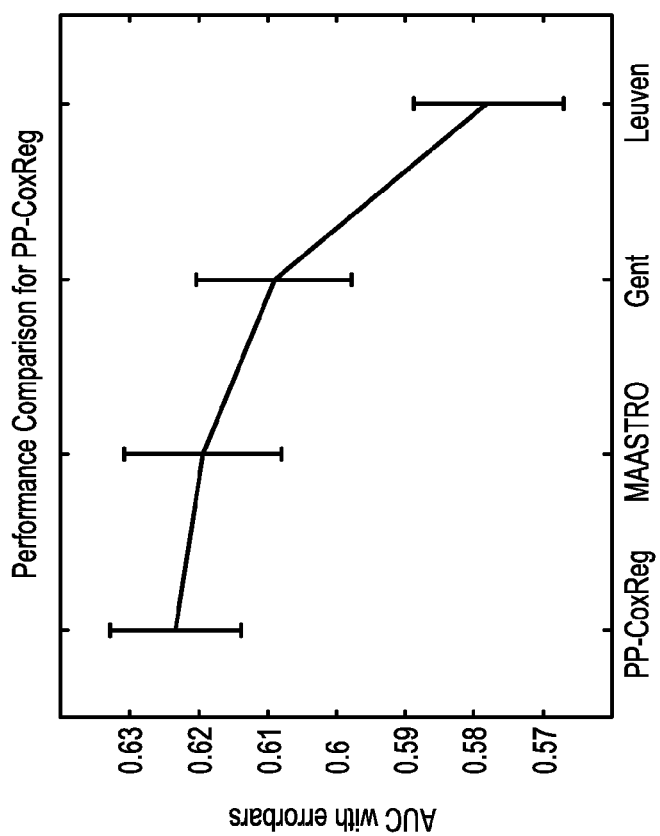

FIG. 5 depicts an AUC comparison results for privacy preserving Cox regression models according to embodiments of the invention with 40% (left) and 60% (right) training patients. The error bars are calculated based on 100 times of random splits of the data. They have the same trend as we have seen in FIG. 3, but it is interesting that with a higher percentage of training data (e.g., 60% on the right), a PPCoxReg according to an embodiment of the invention performs the same as the model trained using only MAASTRO training patients. This indicates a PPCoxReg model according to an embodiment of the invention is more sensitive to the different characteristics of the data from different centers. In practice, one needs to carefully investigate the different data distributions to estimate the benefits of combining them.

Figure 6:
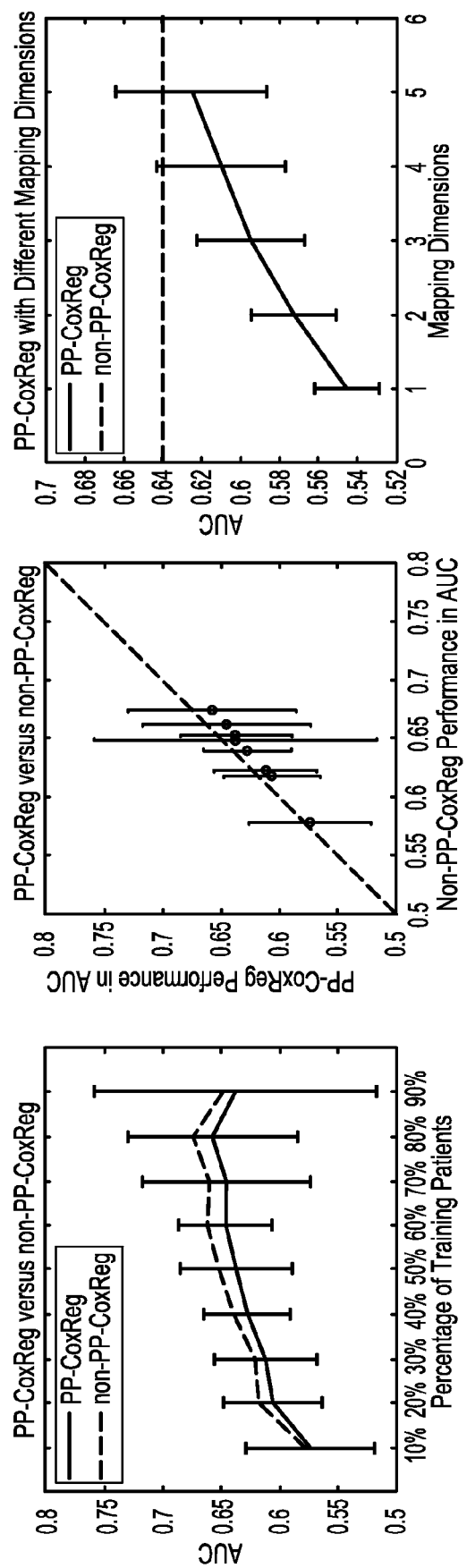
FIG. 6 presents AUC comparison results between a PP-CoxReg according to an embodiment of the invention and non PP-CoxReg models.

FIG. 6 presents AUC comparison results between a PP-CoxReg according to an embodiment of the invention and non PP-CoxReg, which explicitly use all the training data from different centers, and thus upper-bound the predictive performance of a PP-CoxReg according to an embodiment of the invention. The results are compared with different percentages of training patients (left), in a scatter plot (middle), and with different dimensions $\tilde{m}$ for a PP-CoxReg according to an embodiment of the invention (right) in a 40% split. As can be seen, the gaps between a PP-CoxReg according to an embodiment of the invention and non PP-CoxReg models are even smaller those between a PP-SVM according to an embodiment of the invention and non PP-SVM models, meaning PPCoxReg models according to embodiments of the invention are more accurate with respect to the non-privacy preserving solutions. In practice one still needs to choose $\tilde{m}=n-1$ to maximize PP-CoxReg performance, and to choose the best B matrix if possible.

System Implementation

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 7:
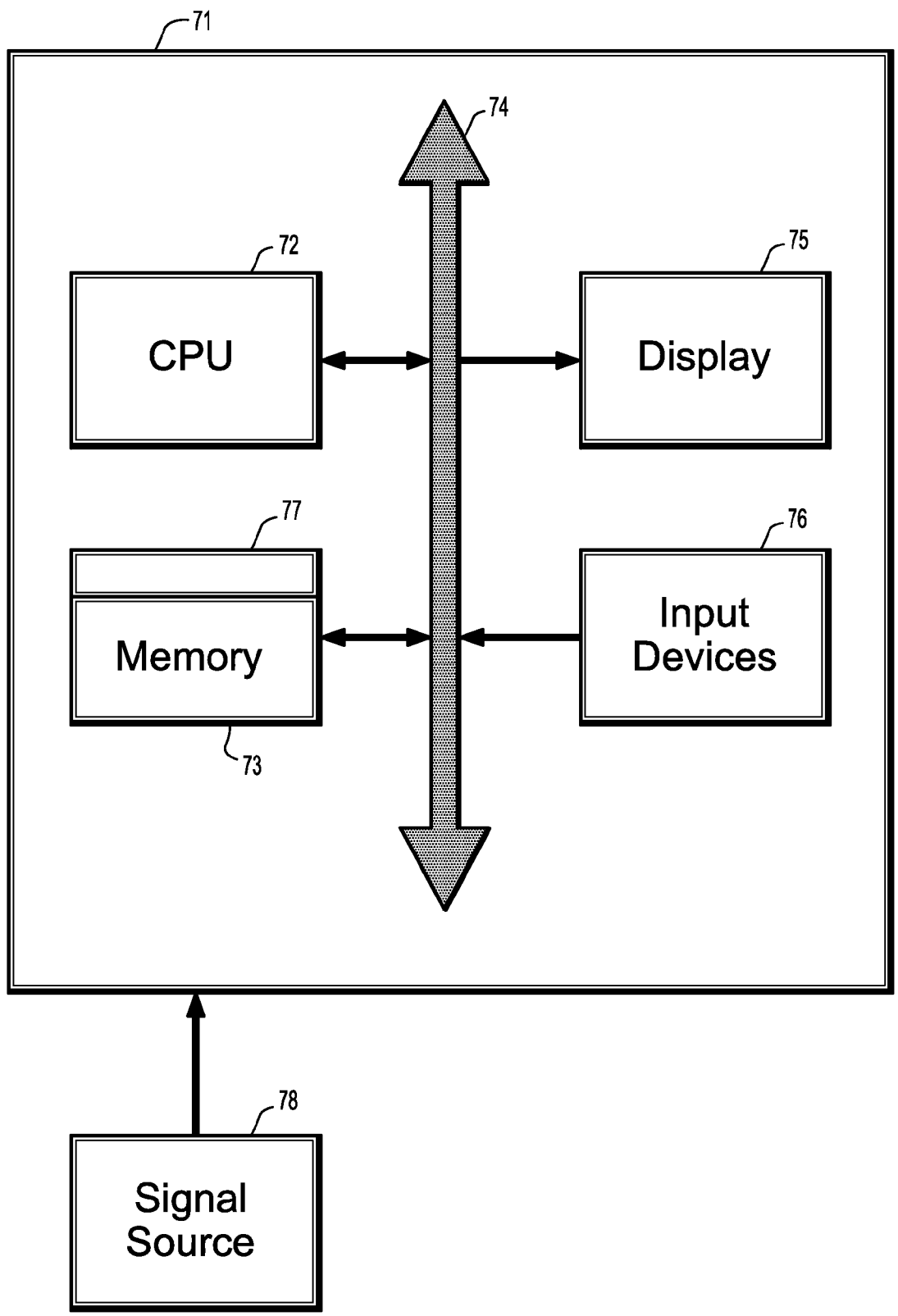
FIG. 7 is a block diagram of an exemplary computer system for implementing a method for privacy preserving data mining, according to an embodiment of the invention.

FIG. 7 is a block diagram of an exemplary computer system for implementing a privacy preserving medical classification techniques according to an embodiment of the invention. Referring now to FIG. 7, a computer system 71 for implementing the present invention can comprise, inter alia, a central processing unit (CPU) 72, a memory 73 and an input/output (I/O) interface 74. The computer system 71 is generally coupled through the I/O interface 74 to a display 75 and various input devices 76 such as a mouse and a keyboard. The support circuits can include circuits such as cache, power supplies, clock circuits, and a communication bus. The memory 73 can include random access memory (RAM), read only memory (ROM), disk drive, tape drive, etc., or a combinations thereof. The present invention can be implemented as a routine 77 that is stored in memory 73 and executed by the CPU 72 to process the signal from the signal source 78. As such, the computer system 71 is a general purpose computer system that becomes a specific purpose computer system when executing the routine 77 of the present invention.

The computer system 71 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer-implemented method for privacy-preserving data mining to determine cancer survival rates, said method comprising the steps of:

providing a random matrix B agreed to by a plurality of entities, wherein each entity i possesses a data matrix $A_i$ of cancer survival data that is not publicly available;

providing a class matrix $D_i$ for each of the data matrices $A_i$;

providing a kernel $K(A_i, B)$ by each of said plurality of entities to allow public computation of a full kernel; and computing, with a computer system, a binary classifier that incorporates said public full kernel, wherein said classifier is adapted to classify a new data vector according to a sign of said classifier, wherein computing comprises:

extracting covariates x from the data matrix $A_i$; and maximizing a quantity $w'K(x, B')$ to solve for vector w, wherein said quantity $w'K(x, B')$ is an effect parameter in a survival model that characterizes an effect on said cancer survival rates.

2. The method of claim 1, wherein said class matrix D is of size m×m wherein in is a number of data points and has a value +1 on a main diagonal for each survival datum that exceeds a predetermined number of years, and has a value of −1 on said main diagonal for each survival datum that does not exceed the predetermined number of years.

3. The method of claim 1, wherein said random matrix B is real valued of size m̂×n, wherein n is a dimensionality of each data point, and m̂<n, and each data matrix $A_i$ is of size m×n, wherein m is a number of data points.

4. The method of claim 1, wherein said full kernel is $$K(A, B') = K\left(\begin{bmatrix} A_1 \\ A_2 \\ \vdots \\ A_q \end{bmatrix}, B\right) = \begin{bmatrix} K(A_1, B) \\ K(A_2, B) \\ \vdots \\ K(A_q, B) \end{bmatrix},$$

where q is a number of entities.

5. The method of claim 1, wherein said classifier is defined as $K(x',B')w−\gamma=0$ wherein w is a vector normal to a hyperplane separating the two classes of the binary classifier, γ determines the location of the separating hyperplane relative to the origin, and K(x', B') is a row vector of K(A, B').

6. The method of claim 5, wherein the classifier is solved for using a Newton-Lagrangian method wherein a square of a 2-norm of a slack variable is minimized with weight v/2 wherein v>0 and a distance between bounding planes is measured in an (n+1)-dimensional space of $(w,\gamma) \in R^{n+1}$.

7. A computer-implemented method for privacy-preserving data mining to determine cancer survival rates, said method comprising the steps of:
providing a random matrix B agreed to by a plurality of entities, wherein each entity i possesses a data matrix $A_i$ of cancer survival rates that is not publicly available;
providing a kernel $K(A_i, B)$ by each of said plurality of entities to allow public computation of a full kernel; and
maximizing a quantity w'K(x,B') wherein x is a row in one of said data matrices $A_i$ to solve for vector w, wherein said quantity w'K(x,B') is an effect parameter in a survival model that characterizes an effect on said cancer survival rates.

8. The method of claim 7, where said effect parameter w'K(x,B') is an effect parameter of a cox regression model log h(t)=α(t)+w'×B', wherein h(t) is a hazard function and α(t) represents an unspecified baseline hazard function.

9. The method of claim 7, wherein said random matrix B is real valued of size m̂×n, wherein n is a dimensionality of each data point, and m̂<n, and each data matrix $A_i$ is of size m×n, wherein m is a number of data points.

10. The method of claim 7, wherein said full kernel is $$K(A, B') = K\left(\begin{bmatrix} A_1 \\ A_2 \\ \vdots \\ A_q \end{bmatrix}, B\right) = \begin{bmatrix} K(A_1, B) \\ K(A_2, B) \\ \vdots \\ K(A_q, B) \end{bmatrix},$$

where q is a number of entities.

11. A program storage device readable by a computer, tangibly embodying a program of instructions executable by the computer to perform the method steps for privacy-preserving data mining to determine cancer survival rates, said method comprising the steps of:
providing a random matrix B agreed to by a plurality of entities, wherein each entity i possesses a data matrix $A_i$ of cancer survival data that is not publicly available;
providing a class matrix $D_i$ for each of the data matrices $A_i$;
providing a kernel $K(A_i, B)$ by each of said plurality of entities to allow public computation of a full kernel; and
computing a binary classifier that incorporates said public full kernel, wherein said classifier is adapted to classify a new data vector according to a sign of said classifier, wherein computing comprises:
extracting covariates x from the data matrix $A_i$, and
maximizing a quantity w'K(x,B') to solve for vector w, wherein said quantity w'K(x, B') is an effect parameter in a survival model that characterizes an effect on said cancer survival rates.

12. The computer readable program storage device of claim 11, wherein said class matrix D is of size m×m wherein in is a number of data points and has a value +1 on a main diagonal for each survival datum that exceeds a predetermined number of years, and has a value of −1 on said main diagonal for each survival datum that does not exceed the predetermined number of years.

13. The computer readable program storage device of claim 11, wherein said random matrix B is real valued of size m̂×n, wherein n is a dimensionality of each data point, and m̂<n, and each data matrix $A_i$ is of size m×n, wherein in is a number of data points.

14. The computer readable program storage device of claim 11, wherein said full kernel is $$K(A, B') = K\left(\begin{bmatrix} A_1 \\ A_2 \\ \vdots \\ A_q \end{bmatrix}, B\right) = \begin{bmatrix} K(A_1, B) \\ K(A_2, B) \\ \vdots \\ K(A_q, B) \end{bmatrix},$$

where q is a number of entities.

15. The computer readable program storage device of claim 11, wherein said classifier is defined as $K(x',B')w−\gamma=0$ wherein w is a vector normal to a hyperplane separating the two classes of the binary classifier, γ determines the location of the separating hyperplane relative to the origin, and K(x', B') is a row vector of K(A, B').

16. The computer readable program storage device of claim 15, wherein the classifier is solved for using a Newton-Lagrangian method wherein a square of a 2-norm of a slack variable is minimized with weight v/2 wherein v>0 and a distance between bounding planes is measured in an (n+1)-dimensional space of $(w, \gamma) \in R^{n+1}$.

* * * * *